(12) United States Patent
Sakazaki et al.

(10) Patent No.: US 11,198,234 B2
(45) Date of Patent: Dec. 14, 2021

(54) MOLD CASE AND MANUFACTURING METHOD OF MICRONEEDLE ARRAY

(71) Applicant: FUJIFILM Corporation, Tokyo (JP)

(72) Inventors: Yoshiki Sakazaki, Kanagawa (JP); Kenichiro Tamaki, Kanagawa (JP); Toshihiro Usa, Kanagawa (JP); Ikuo Takano, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 289 days.

(21) Appl. No.: 16/391,341

(22) Filed: Apr. 23, 2019

(65) Prior Publication Data

US 2019/0351588 A1    Nov. 21, 2019

(30) Foreign Application Priority Data

May 16, 2018    (JP) .............................. JP2018-094790

(51) Int. Cl.
*B29C 39/26*    (2006.01)
*B29C 39/02*    (2006.01)
*B29L 31/00*    (2006.01)

(52) U.S. Cl.
CPC ............ *B29C 39/26* (2013.01); *B29C 39/026* (2013.01); *B29K 2883/00* (2013.01);
(Continued)

(58) Field of Classification Search
CPC .................. B29C 39/26; B29C 39/026; B29L 2031/7544; B29L 2031/756;
(Continued)

(56) References Cited

U.S. PATENT DOCUMENTS

| 5,525,226 A * | 6/1996 | Brown | F16J 15/061 |
| | | | 277/641 |
| 2006/0097423 A1* | 5/2006 | Aversenti | B29C 70/34 |
| | | | 264/236 |

(Continued)

FOREIGN PATENT DOCUMENTS

| CN | 107984663 | 5/2018 |
| JP | 2009241357 | 10/2009 |

(Continued)

OTHER PUBLICATIONS

"Search Report of Europe Counterpart Application", dated Nov. 14, 2019, p. 1-p. 9.

(Continued)

Primary Examiner — Francisco W Tschen
Assistant Examiner — Elisa H Vera
(74) Attorney, Agent, or Firm — JCIPRNET

(57) ABSTRACT

Provided are a mold case that prevents deformation of a microneedle array, and a manufacturing method of a microneedle array. The problems are solved by the manufacturing method of a microneedle array including: a filling step of filling needle-like recessed portions of a mold having flexibility and having a plurality of the needle-like recessed portions on a front surface, with a liquid material; and a drying step of drying the liquid material in a state where the mold filled with the liquid material is stored in the mold case which causes an edge portion of the mold to be sandwiched between the lid and the pedestal.

12 Claims, 18 Drawing Sheets

(52) U.S. Cl.
CPC ............... *B29K 2995/0065* (2013.01); *B29L 2031/756* (2013.01); *B29L 2031/7544* (2013.01)

(58) Field of Classification Search
CPC ...... A61M 37/0015; A61M 2037/0023; A61M 2037/0046; A61M 2037/0053; Y10S 277/925
See application file for complete search history.

(56) References Cited

U.S. PATENT DOCUMENTS

| | | | |
|---|---|---|---|
| 2009/0234301 A1 | 9/2009 | Tomono | |
| 2010/0209764 A1 | 8/2010 | Heo et al. | |
| 2010/0289260 A1* | 11/2010 | Morton | F16L 37/18 285/312 |
| 2016/0254623 A1* | 9/2016 | Creusen | H01R 24/62 439/366 |
| 2018/0250851 A1 | 9/2018 | Ogawa et al. | |
| 2018/0333898 A1* | 11/2018 | Francis | B29C 33/40 |

FOREIGN PATENT DOCUMENTS

| | | |
|---|---|---|
| JP | 2013-074924 | 4/2013 |
| JP | 2014018507 | 2/2014 |
| WO | 2008062832 | 5/2008 |
| WO | 2017056895 | 4/2017 |

OTHER PUBLICATIONS

"Office Action of Japan Counterpart Application", dated Jun. 2, 2021, with English translation thereof, pp. 1-6.

* cited by examiner

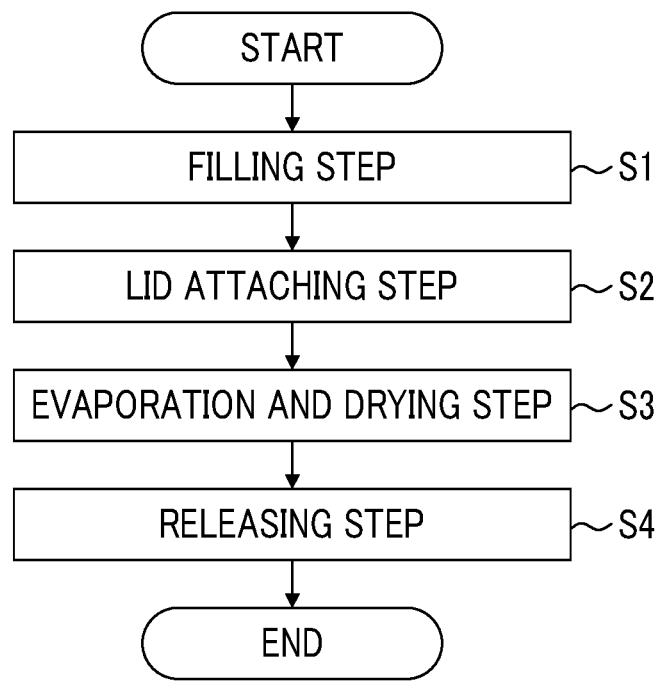
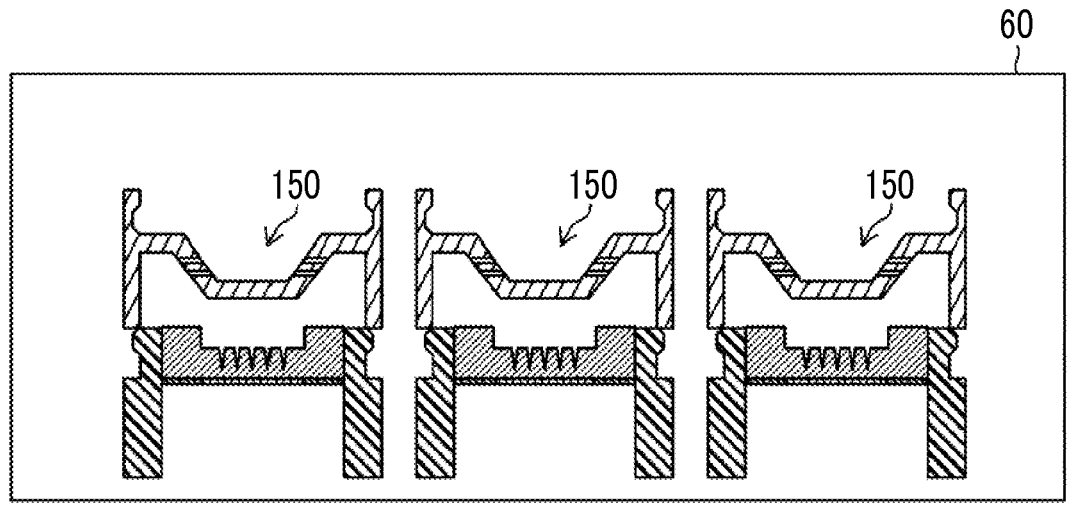

FIG. 20
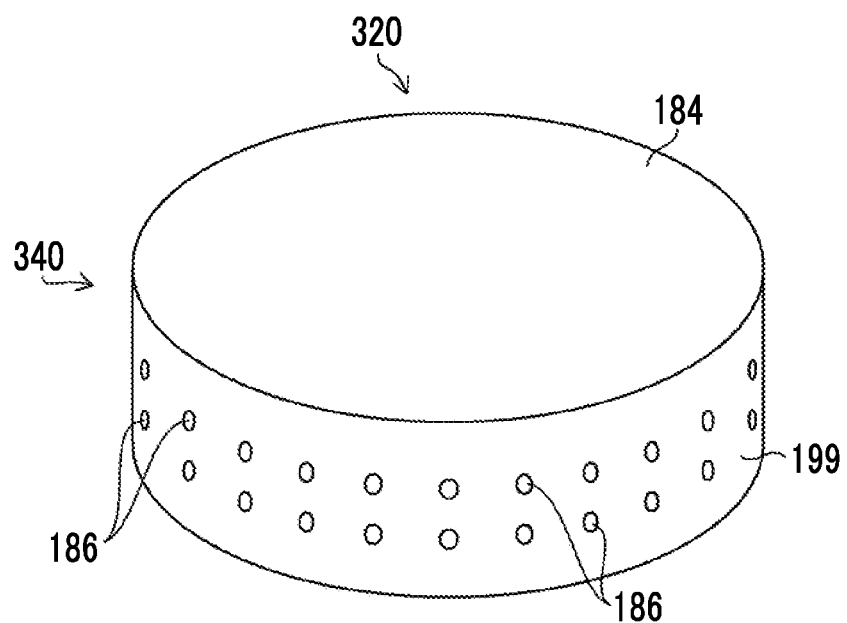
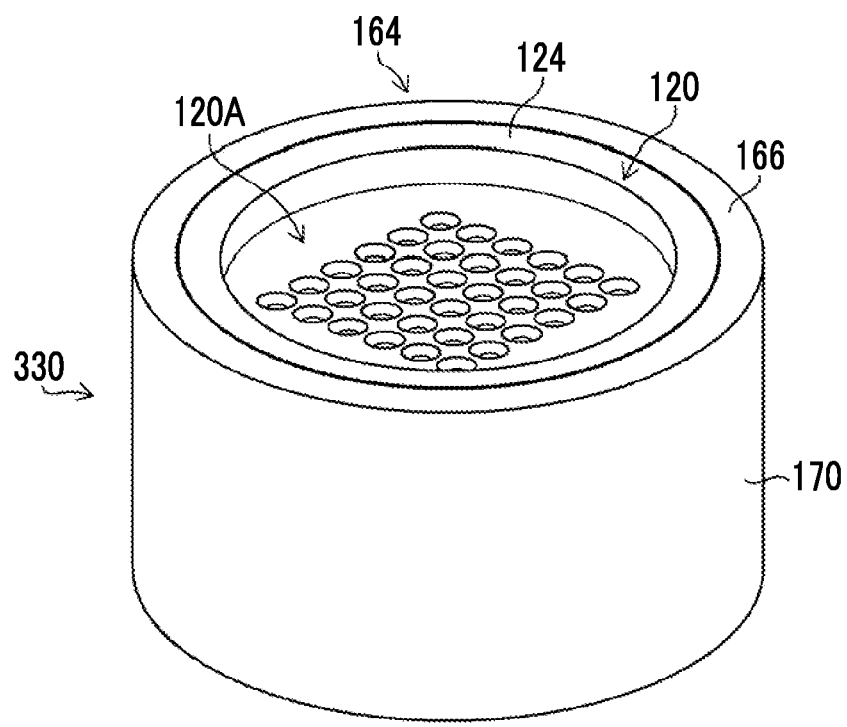
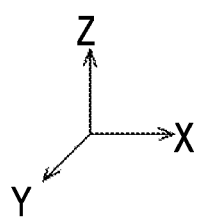

MOLD CASE AND MANUFACTURING METHOD OF MICRONEEDLE ARRAY

CROSS-REFERENCE TO RELATED APPLICATION

The present application claims priority under 35 U.S.C § 119(a) to Japanese Patent Application No. 2018-094790 filed on May 16, 2018, which is hereby expressly incorporated by reference, in its entirety, into the present application.

BACKGROUND OF THE INVENTION

1. Field of the Invention

The present invention relates to a mold case and a manufacturing method of a microneedle array, and more particularly to a technique for manufacturing a microneedle array by drying a liquid filling a needle-like recessed portion of a mold.

2. Description of the Related Art

In recent years, as a novel dosage form capable of injecting drugs such as insulin, vaccines, and human growth hormone (hGH) into the skin without pain, a microneedle array has been known. The microneedle array is an array of microneedles (also referred to as fine needles or small needles) which contain drugs and are biodegradable. By attaching this microneedle array to the skin, each microneedle pierces the skin, and these microneedles are absorbed in the skin such that the drugs contained in each microneedle can be administered into the skin. Microneedle arrays are also called percutaneous absorption sheets.

Various suggestions have been made as a manufacturing method of a microneedle array having a fine pattern as described above. JP2013-074924A discloses manufacturing a microneedle array by preparing a mold having a plurality of conical recessed portions, filling the recessed portions with a needle raw material, drying the filled raw material so as to solidify, and releasing the resultant from the mold.

SUMMARY OF THE INVENTION

By using the mold made of rubber or the like having high flexibility, the microneedle array can be easily released after drying. However, with the mold having flexibility, there may be cases where the microneedle array itself deforms in such a manner as to draw the mold as drying of the filled liquid material proceeds, and there is a problem that the microneedle array cannot be manufactured into an intended shape.

The present invention has been made taking the above circumstances into consideration, and an object thereof is to provide a mold case capable of preventing deformation of a microneedle array, and a manufacturing method of a microneedle array.

In order to achieve the object, an aspect of a mold case is a mold case including: a pedestal which supports a rear surface of a mold that has flexibility and has a plurality of needle-like recessed portions on a front surface; and a lid which is attachable to and detachable from the pedestal and covers the front surface of the mold, in which the lid causes an edge portion of the mold to be sandwiched between the lid and the pedestal.

According to the aspect, since the rear surface of the mold having flexibility is supported by the pedestal and the edge portion of the mold is sandwiched between the lid which is a member attachable to and detachable from the pedestal and covers the front surface of the mold and the pedestal, deformation of a microneedle array can be prevented.

It is preferable that the pedestal includes a seating surface portion on which the mold is placed, and the lid includes a mold fixing portion at least a part of which is parallel to and faces the seating surface portion. Accordingly, the edge portion of the mold can be sandwiched between the mold fixing portion and the seating surface portion.

It is preferable that the mold fixing portion abuts the mold over an entire circumference of the edge portion of the mold. Accordingly, deformation of the mold can be appropriately prevented.

It is preferable that the lid includes a cover portion which is connected to the mold fixing portion and forms a space between the cover portion and the plurality of needle-like recessed portions. Accordingly, the front surface of the mold can be appropriately covered.

It is preferable that the pedestal includes a side wall portion which is erected on the seating surface portion and surrounds the mold placed on the seating surface portion. By defining the placement position of the mold by the side wall portion, the edge portion of the mold can be appropriately sandwiched.

It is preferable that the side wall portion is erected to be a height lower than a thickness of the mold. By providing the side wall portion to be erected to be such a height, the edge portion can be mold can be appropriately sandwiched.

It is preferable that a fixed engagement portion provided on an outer peripheral surface of the side wall portion of the pedestal and an elastic engagement portion provided in the mold fixing portion of the lid are further included, and the pedestal and the lid are fixed to each other by snap-fit engagement between the fixed engagement portion and the elastic engagement portion. The lid can be appropriately fixed to the pedestal by the snap-fit engagement.

It is preferable that in the lid, a hinge lever that releases the snap-fit engagement is provided in the mold fixing portion. Using the hinge lever, the snap-fit engagement can be appropriately released.

It is preferable that the lid includes a tubular portion connected to the mold fixing portion, and the tubular portion and the side wall portion are brought into contact with each other to be fitted and fixed to each other. By the fitting and fixing, the lid can be appropriately fixed to the pedestal. The inner periphery of the tubular portion and the outer periphery of the side wall portion may be brought into contact with each other, or the outer periphery of the tubular portion and the inner periphery of the side wall portion may be brought into contact with each other.

It is preferable that the side wall portion and the mold fixing portion are screwed and fixed to each other. By the screwing and fixing, the lid can be appropriately fixed to the pedestal. A male threaded portion provided in the outer periphery of the side wall portion and a female threaded portion provided in the inner periphery of the mold fixing portion may be screwed and fixed to each other, or a female threaded portion provided in the inner periphery of the side wall portion and a male threaded portion provided in the outer periphery of the mold fixing portion may be screwed and fixed to each other.

The lid may have a mass of 4 grams or more, and the lid may be supported by the edge portion of the mold. By supporting the lid by the edge portion of the mold, the edge portion of the mold can be sandwiched between the lid and the pedestal.

It is preferable that the mold has a bank portion provided at the edge portion of the front surface, and the lid causes the bank portion of the mold to be sandwiched between the lid and the pedestal. By including the bank portion in the mold, the edge portion of the mold can be appropriately sandwiched.

In order to achieve the object, an aspect of a manufacturing method of a microneedle array is a manufacturing method of a microneedle array including: a filling step of filling needle-like recessed portions of a mold having flexibility and having a plurality of the needle-like recessed portions on a front surface, with a liquid material; and a drying step of drying the liquid material in a state where the mold filled with the liquid material is stored in a mold case which causes an edge portion of the mold to be sandwiched between a lid and a pedestal.

According to the aspect, since the liquid material is dried in a state where the edge portion of the mold filled with the liquid material is sandwiched, deformation of the microneedle array in the drying step can be prevented.

According to the present invention, deformation of a microneedle array can be prevented.

BRIEF DESCRIPTION OF THE DRAWINGS

FIG. 9 is a flowchart showing each step of a manufacturing method of the percutaneous absorption sheet.

FIG. 10 is a schematic view illustrating a sterilization process.

FIG. 20 is a perspective view illustrating the pedestal on which the mold is placed, and a lid.

DESCRIPTION OF THE PREFERRED EMBODIMENTS

Figure 1:
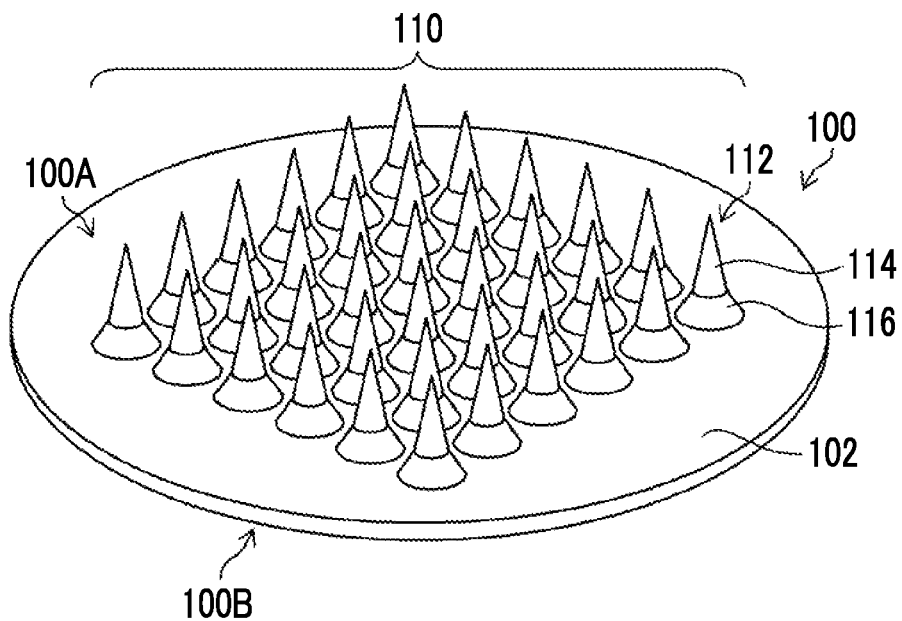
FIG. 1 is a perspective view illustrating an example of a percutaneous absorption sheet.

Hereinafter, preferred embodiments of the present invention will be described with reference to the accompanying drawings. The present invention is described by the following preferred embodiments. Modifications can be made by various methods without departing from the scope of the present invention, and other embodiments than this embodiment can also be used. Therefore, all modifications within the scope of the present invention are included in the appended claims.

Here, in the figures, like elements having similar functions are denoted by like reference numerals. In addition, in this specification, in a case where a numerical value range is expressed using "to", the numerical value range includes the numerical values of the upper limit and the lower limit indicated by "to".

Configuration of Percutaneous Absorption Sheet

First, an example of a microneedle array (percutaneous absorption sheet) will be described.

FIG. 1 is a perspective view illustrating an example of a percutaneous absorption sheet 100. The percutaneous absorption sheet 100 of this embodiment corresponds to a patch for one administration. The percutaneous absorption sheet 100 has a front surface 100A and a rear surface 100B, and is made up of a sheet-like sheet portion 102 and a protruding pattern 110.

The term "sheet-like" means a thin flat shape as a whole with respect to two opposed front and rear surfaces 100A and 100B having a large area, and it is not necessary that the front surface 100A and the rear surface 100B are perfectly flat. In addition, although the sheet portion 102 illustrated in FIG. 1 is circular in a plan view, the sheet portion 102 may be rectangular, polygonal, elliptical, or the like.

The protruding pattern 110 has a plurality of needle-like protruding portions 112 containing a drug. The needle-like protruding portions 112 are provided on the front surface 100A. The needle-like protruding portion 112 is constituted by a needle portion 114, and a frustum portion 116 with which the needle portion 114 and the sheet portion 102 are connected.

On the front surface 100A of the percutaneous absorption sheet 100, a plurality of the frustum portions 116 are disposed. The frustum portion 116 has two bottom surfaces and has a three-dimensional structure surrounded by a conical surface. The bottom surface (lower bottom surface) of the two bottom surfaces of the frustum portion 116 having a large area is connected to the sheet portion 102. The bottom surface (upper bottom surface) of the two bottom surfaces of the frustum portion 116 having a small area is connected to the needle portion 114. That is, of the two bottom surfaces of the frustum portion 116, the area of the bottom surfaces in a direction away from the sheet portion 102 is small.

The needle portion 114 has a bottom surface with a large area and a shape having a narrowest area at the distal end apart from the bottom surface. Since the bottom surface of the needle portion 114 having a large area is connected to the upper bottom surface of the frustum portion 116, the needle portion 114 has a tapered shape in a direction away from the frustum portion 116. Therefore, the needle-like protruding portion 112 constituted by the needle portion 114 and the frustum portion 116 has a tapered shape as a whole from the sheet portion 102 toward the distal end. The plurality of, for example, 4 to 2500 needle-like protruding portions 112 are provided on the sheet portion 102. However, the number of needle-like protruding portions 112 is not limited thereto.

In FIG. 1, the frustum portion 116 has a truncated cone shape, and the needle portion 114 has a cone shape. The shape of the distal end of the needle portion 114 can be appropriately changed to a curved surface having a radius of curvature of 0.01 μm or more and 50 μm or less, a flat surface, or the like according to the degree of insertion of the needle portion 114 into the skin.

Configuration of Mold

Figure 2:
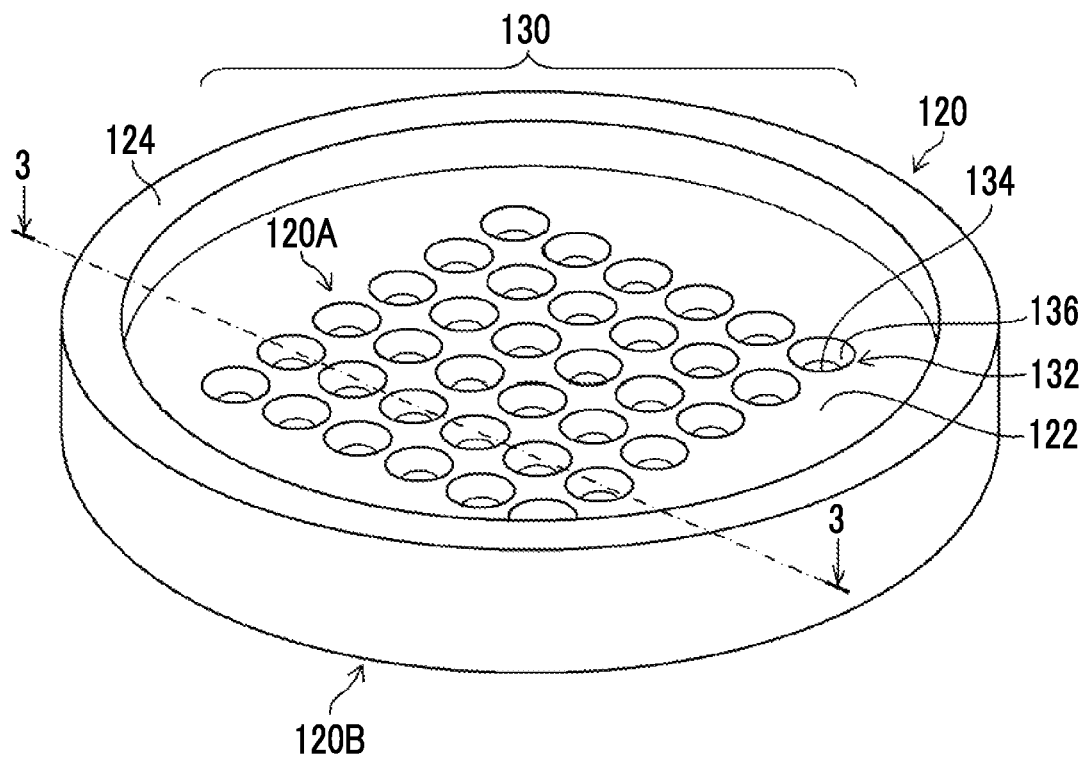
FIG. 2 is a perspective view illustrating an example of a mold.
Figure 3:
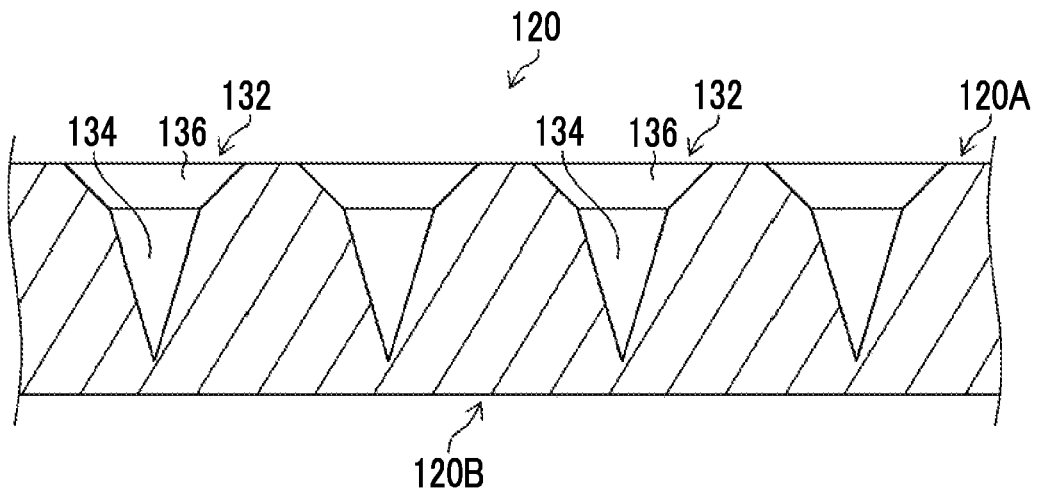
FIG. 3 is a partially enlarged view of a section taken along the cross section 3-3 in FIG. 2.

FIG. 2 is a perspective view illustrating an example of a mold 120 for manufacturing (molding) the percutaneous absorption sheet 100. FIG. 3 is a partially enlarged view of a section taken along the cross section 3-3 in FIG. 2. The mold 120 has a front surface (front surface) 120A and a rear surface 120B, and is constituted by a flat portion 122, a bank portion 124, and a recessed portioned pattern 130.

The flat portion 122 has a flat shape corresponding to the sheet portion 102 of the percutaneous absorption sheet 100. The bank portion 124 is erected on the peripheral portion of the front surface 120A and surrounds the flat portion 122. The width of the bank portion 124 in the radial direction of the mold 120 is preferably 1.5 mm or more. Since the rear surface 120B is flat, the thickness of the bank portion 124 of the mold 120 is larger than the thickness of the flat portion 122.

The recessed portioned pattern 130 is constituted by a plurality of needle-like recessed portions 132 provided in the flat portion 122. The needle-like recessed portion 132 has a shape corresponding to the needle-like protruding portion 112 of the percutaneous absorption sheet 100, and is constituted by a distal end recessed portion 134 corresponding to the needle portion 114 and a cup portion 136 corresponding to the frustum portion 116.

The distal end recessed portion 134 has a tapered shape in the depth direction (thickness direction) of the mold 120. The distal end recessed portion 134 may have a diameter of 150 μm to 500 μm and a height of 150 μm to 2000 μm. The cup portion 136 is provided with an opening at the front surface 120A of the mold 120, has a shape that narrows in the depth direction of the mold 120, and is connected to the distal end recessed portion 134 at the narrowest portion. The cup portion 136 may have a diameter of 500 μm to 1000 μm and a height of 100 μm to 500 μm.

The shape of the needle-like recessed portion 132 is not limited to this example. A shape provided with an intermediate recessed portion having a constant width in the depth direction, such as a cylinder, a square prism, or a polygonal prism may be provided between the distal end recessed portion 134 and the cup portion 136. Furthermore, a through-hole that reaches the rear surface 120B and penetrates the mold 120 may be formed at the distal end of the tapered shape. The arrangement, pitch, number, and the like of the needle-like recessed portions 132 may be determined according to the arrangement, pitch, number, and the like of the needle-like protruding portions 112 necessary for the percutaneous absorption sheet 100.

The material used for the mold 120 is preferably a material having flexibility, and more preferably a material having high gas permeability.

Oxygen permeability, which is representative of gas permeability, is preferably larger than $1\times10^{-12}$ (mL/s·m·Pa), and more preferably $1\times10^{-10}$ (mL/s·m·Pa). By manufacturing the mold 120 with a material having high gas permeability, a liquid filling the needle-like recessed portion 132 can be suctioned by suction from the rear surface 120B of the mold 120 such that filling of the inside of the needle-like recessed portion 132 can be accelerated. In addition, the air existing in the needle-like recessed portion 132 can be removed from the rear surface 120B side. Accordingly, the percutaneous absorption sheet 100 with fewer defects can be manufactured.

Specific examples of such materials include those obtained by melting or dissolving, in a solvent, general engineering plastics such as silicone resins (for example, SYLGARD 184 (registered trademark) manufactured by Dow Corning Corporation, 1310ST manufactured by Shin-Etsu Chemical Co., Ltd.), ultraviolet-curable resins, polystyrene resins, polymethyl methacrylate resins, epoxy resins, polyethylene terephthalate resins, polyoxymethylene resins, polytetrafluoroethylene resins, polyethylene resins, phenol resins, and urethane resins.

Among these, silicone rubber-based materials are durable against transfer by repeated pressurization, have good releasability from materials, and thus can be suitably used.

Configuration of Mold Case (First Embodiment)

Figure 4:
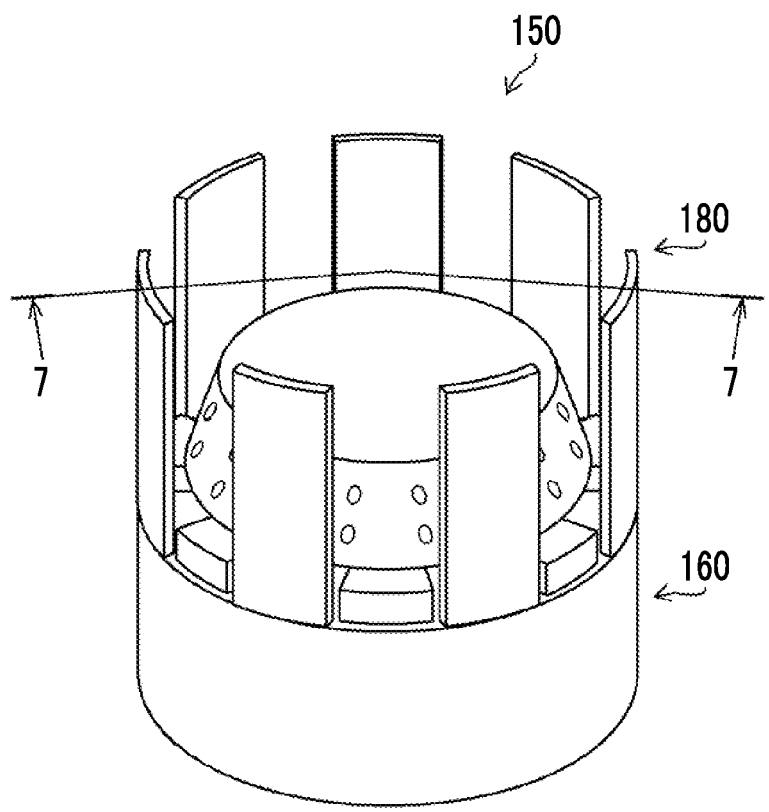
FIG. 4 is a perspective view of a mold case.

FIG. 4 is a perspective view of a mold case 150 for handling the percutaneous absorption sheet 100. The mold case 150 includes a pedestal 160 and a lid 180 attachable to and detachable from the pedestal 160.

Figure 5:
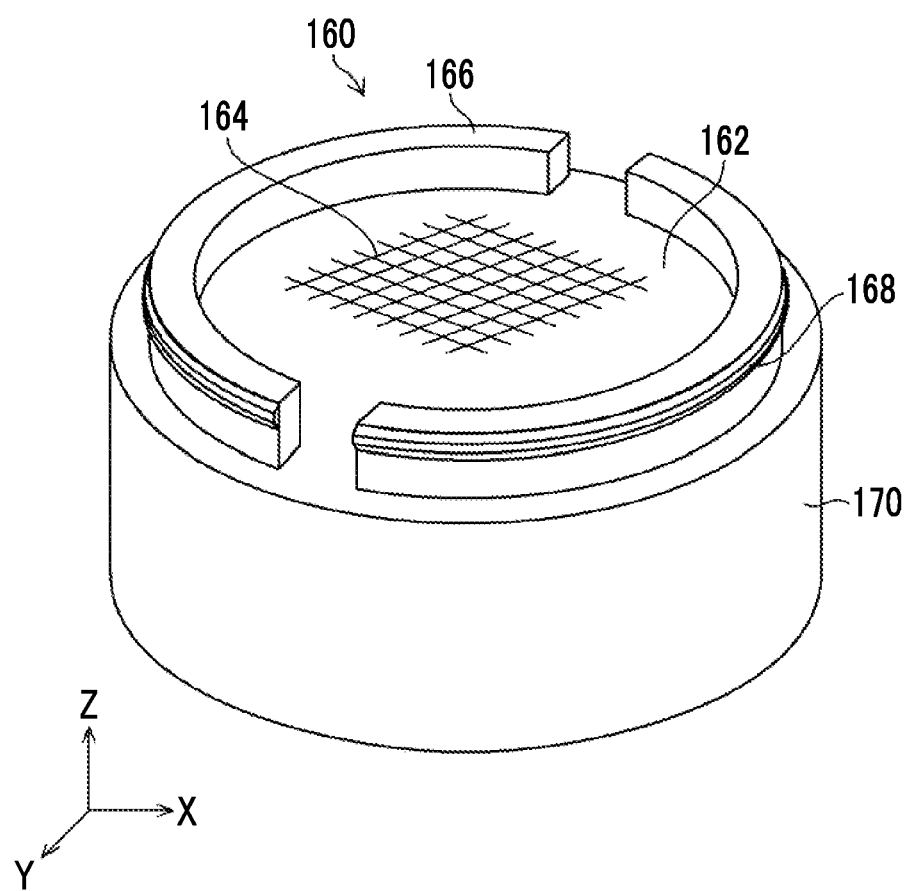
FIG. 5 is a perspective view of pedestal.

FIG. 5 is a perspective view of the pedestal 160. The pedestal 160 is made of polypropylene, polyethylene, an acrylonitrile butadiene styrene (ABS) resin, or the like. The pedestal 160 is produced by injection molding. Alternatively, the pedestal 160 can also be produced by machining metal such as steel use stainless (SUS). The pedestal 160 includes a seating surface portion 162, a ventilation portion 164, a side wall portion 166, a fixed engagement portion 168, and a base portion 170.

The seating surface portion 162 is a thin plate-like member which is circular in a plan view in the Z direction. The seating surface portion 162 supports the rear surface 120B of the mold 120 placed on the pedestal 160. The ventilation portion 164 is formed in a mesh shape and penetrates the seating surface portion 162 for ventilation. The ventilation portion 164 is disposed at a position corresponding to at least the recessed portioned pattern 130 of the placed mold 120.

The side wall portions 166 are erected on the seating surface portion 162. The side wall portion 166 has a shape in which the external shape of the mold 120 fits, and defines the placement position of the mold 120. In the example illustrated in FIG. 5, in the plan view in the Z direction, two semicircular arc-shaped side wall portions 166 are erected along the periphery of the seating surface portion 162.

The fixed engagement portion 168 is disposed along the outer peripheral surface of the side wall portion 166. The fixed engagement portion 168 is a protruding member protruding from the outer peripheral surface of the side wall portion 166.

The base portion 170 is a cylindrical member and is provided such that the central axis of the cylinder is parallel to the Z direction. The base portion 170 supports the seating surface portion 162 and the side wall portions 166 in a state where the seating surface portion 162 is parallel to the XY plane which is a horizontal plane.

Figure 6:
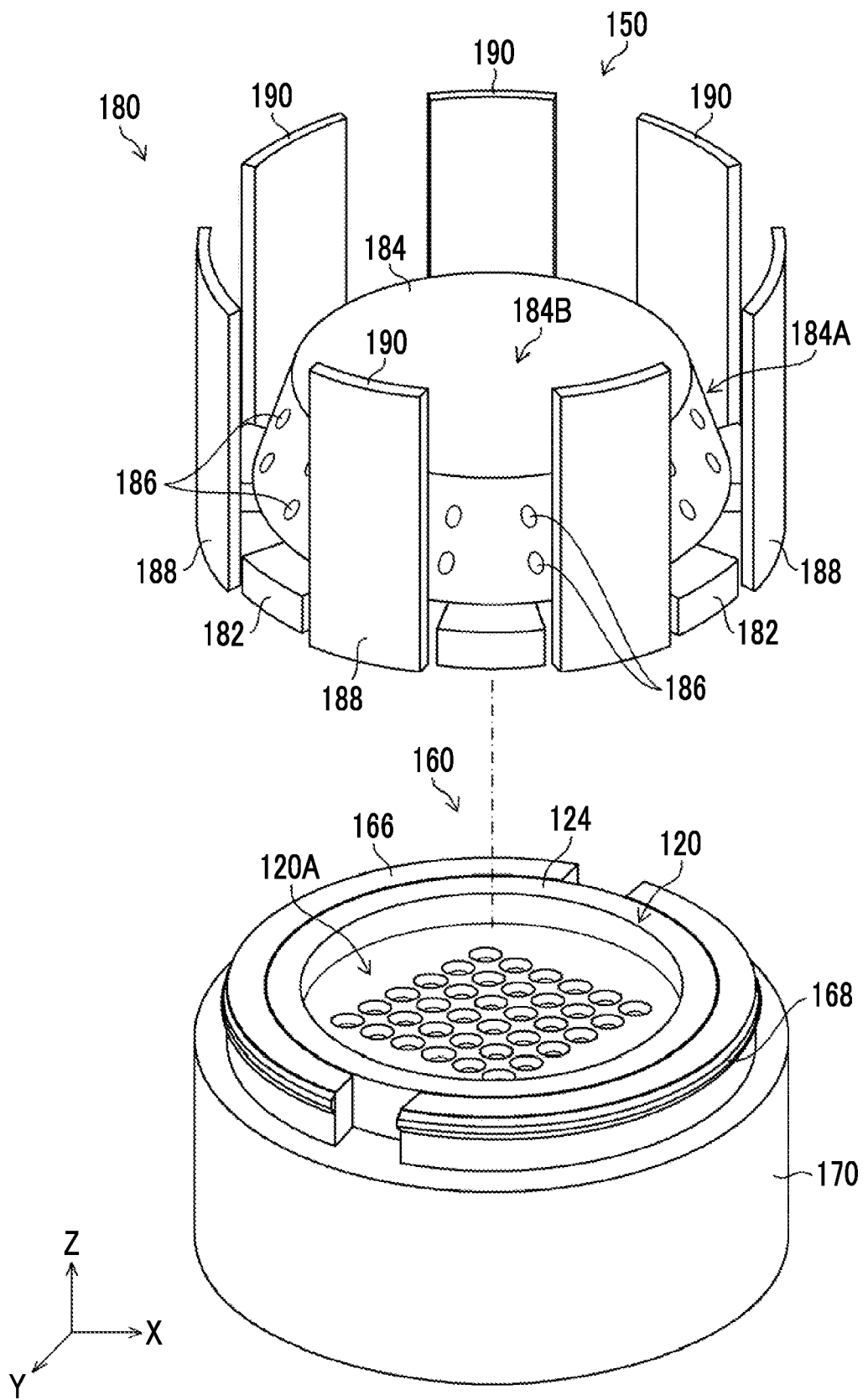
FIG. 6 is a perspective view illustrating the pedestal on which the mold is placed, and a lid.
Figure 7:
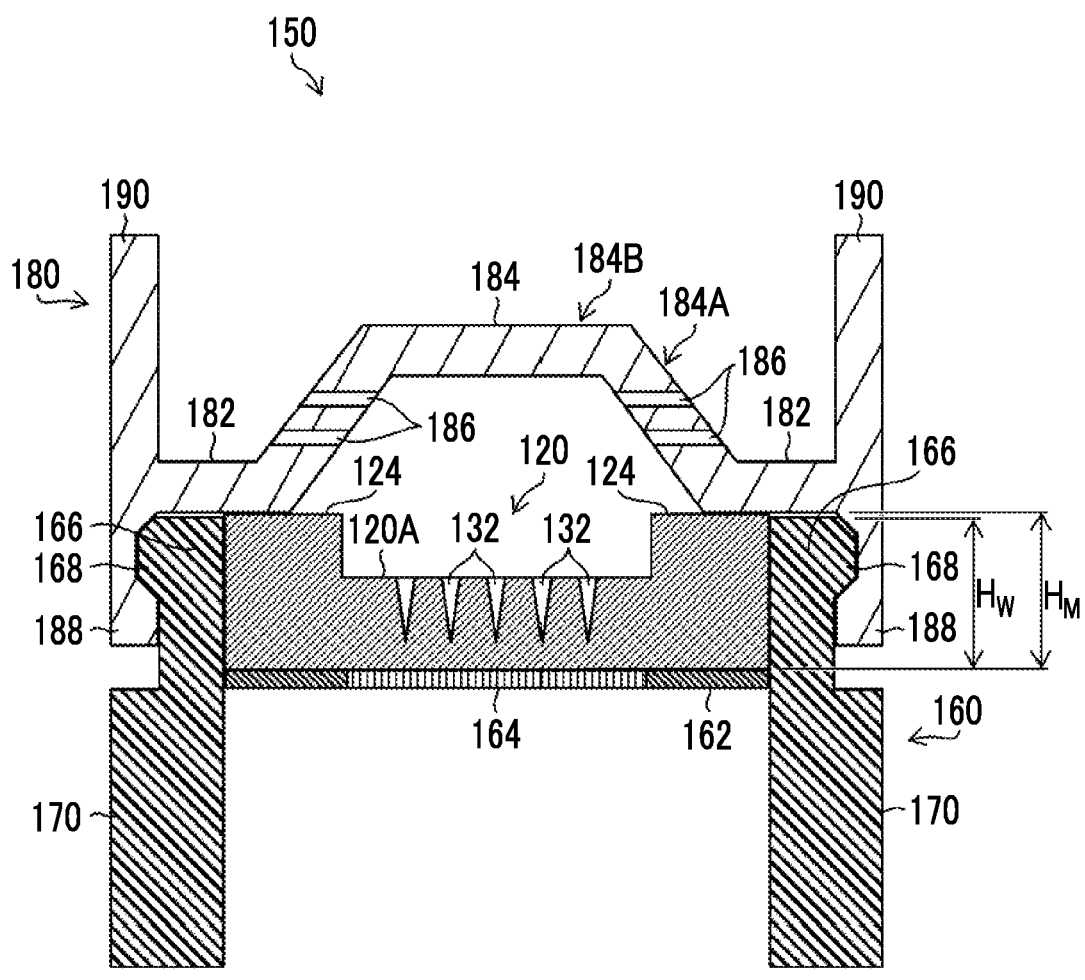
FIG. 7 is a cross-sectional view taken along the line 7-7 in FIG. 4.

FIG. 6 is a perspective view illustrating the pedestal 160 on which the mold 120 is placed, and the lid 180. FIG. 7 is a cross-sectional view taken along the line 7-7 in FIG. 4.

The mold 120 placed on the seating surface portion 162 fits in the side wall portions 166. The mold 120 is supported by the seating surface portion 162 in a state where the front surface 120A is directed upward in the Z direction which is the vertical direction and is parallel to the XY plane. In a state where the mold 120 is placed on the seating surface portion 162, it is preferable that the hole of the ventilation portion 164 of the seating surface portion 162 is disposed at a position immediately below each of the plurality of needle-like recessed portions 132.

The lid 180 is made of polypropylene, polyethylene, an ABS resin or the like. The lid 180 is produced by injection molding. The lid 180 includes a mold fixing portion 182, a cover portion 184, through-holes 186, elastic engagement portions 188, hinge levers 190, and the like.

The mold fixing portion 182 is a ring-shaped thin plate-like member in which a concentric cavity is formed in the center portion in the plan view in the Z direction. In a state where the lid 180 is attached to the pedestal 160, at least a part of the mold fixing portion 182 is disposed parallel to the XY plane and faces the seating surface portion 162.

The cover portion 184 is constituted by a conical surface 184A connected to the ring-shaped inner diameter side of the mold fixing portion 182 and a top surface 184B connected to the conical surface 184A. In a state where the lid 180 is attached to the pedestal 160, the cover portion 184 forms a space between the cover portion 184 and the plurality of needle-like recessed portions 132 provided in the flat portion 122 of the mold 120.

The through-holes 186 are provided in the conical surface 184A of the cover portion 184. The shape, number, size, and arrangement of the through-holes 186 can be appropriately determined according to the conditions of a drying step, which will be described later, and the like. The through-hole 186 is provided parallel to the XY plane. By providing the through-hole 186 parallel to the XY plane, intrusion of dust into the mold case 150 can be suppressed. Accordingly, infiltration and adhesion of dust to the percutaneous absorption sheet 100 can be prevented. The through-holes 186 may also be provided in the top surface 184B of the cover portion 184.

The elastic engagement portions 188 are connected to the outer diameter side of the mold fixing portion 182 and are provided on the side opposite to the cover portion 184 with respect to the mold fixing portion 182. The fixed engagement portion 168 of the pedestal 160 and the elastic engagement portion 188 are members for snap-fit engagement with each other. In order to attach the lid 180 to the pedestal 160, the lid 180 is pushed downward (in the −Z direction) in the vertical direction with respect to the pedestal 160 that supports the mold 120 in parallel to the XY plane. At this time, the elastic engagement portion 188 abut the fixed engagement portion 168 and climb over a step of the fixed engagement portion 168 while deforming in a direction away from the side wall portion 166 by elasticity such that the fixed engagement portion 168 and the elastic engagement portions 188 are engaged with each other in a snap-fit manner.

Here, the elastic engagement portions 188 are provided at seven places, but may also be provided at at least two places.

The side wall portions 166 are erected to be a height lower than the thickness of the mold 120. That is, assuming that the thickness of the mold 120 (the height from the seating surface portion 162 to the upper surface of the bank portion 124 in a case where the mold 120 is placed on the seating surface portion 162) is $H_M$ and the height of the side wall portion 166 from the seating surface portion 162 is $H_W$, the thickness and the height have a relationship of $H_M \geq H_W$.

Furthermore, in a case where the lid 180 is attached to the pedestal 160, at least a part of the mold fixing portion 182 faces the seating surface portion 162. Therefore, in a case where the lid 180 is mounted on the pedestal 160 on which the mold 120 is placed, the part of the mold fixing portion 182 which faces the seating surface portion 162 abuts the entire circumference of the bank portion 124 which is the edge portion of the mold 120. Accordingly, the bank portion 124, which is the edge portion of the mold 120, can be sandwiched between the seating surface portion 162 of the pedestal 160 and the mold fixing portion 182 of the lid 180. Therefore, as will be described later, deformation of the mold 120 can be prevented.

The part that the mold fixing portion 182 abuts is not limited to the bank portion 124, and may be the edge portion of the mold 120. For example, in a case where the mold 120 without the bank portion 124, the mold fixing portion 182 may abut the edge portion of the flat portion 122 other than the recessed portioned pattern 130. In addition, the mold fixing portion 182 is not limited to a form in which the mold fixing portion 182 abuts the entire circumference of the edge portion of the mold 120 but may abut a part of the mold 120.

The hinge levers 190 are connected to the outer diameter side of the mold fixing portion 182 and are provided on the side opposite to the elastic engagement portions 188 while respectively corresponding to the plurality of elastic engagement portions 188. The hinge lever 190 is a member for releasing the snap-fit engagement. To release the lid 180 from the pedestal 160, the hinge levers 190 are deformed in a direction to approach each other. Accordingly, with the hinge levers 190 acting as the force points, the mold fixing portion 182 acting as the fulcrum, and the elastic engagement portions 188 as the action points, the elastic engagement portions 188 are deformed in a direction away from the side wall portion 166. In this state, as the lid 180 are pulled upward in the vertical direction (Z direction) from the fixed pedestal 160, the elastic engagement portions 188 climb over the step of the fixed engagement portion 168, and the engagement with the fixed engagement portion 168 is released, so that the lid 180 is released from the pedestal 160.

Here, the case where the side wall portions 166 are erected to be a height lower than the thickness of the mold 120 has been described. However, in a case where the side wall portions 166 are erected to be a height higher than the thickness of the mold 120, that is, in a case of a relationship of $H_M < H_W$, a protruding portion 182A may be provided in the mold fixing portion 182 as illustrated in FIG. 8.

Figure 8:
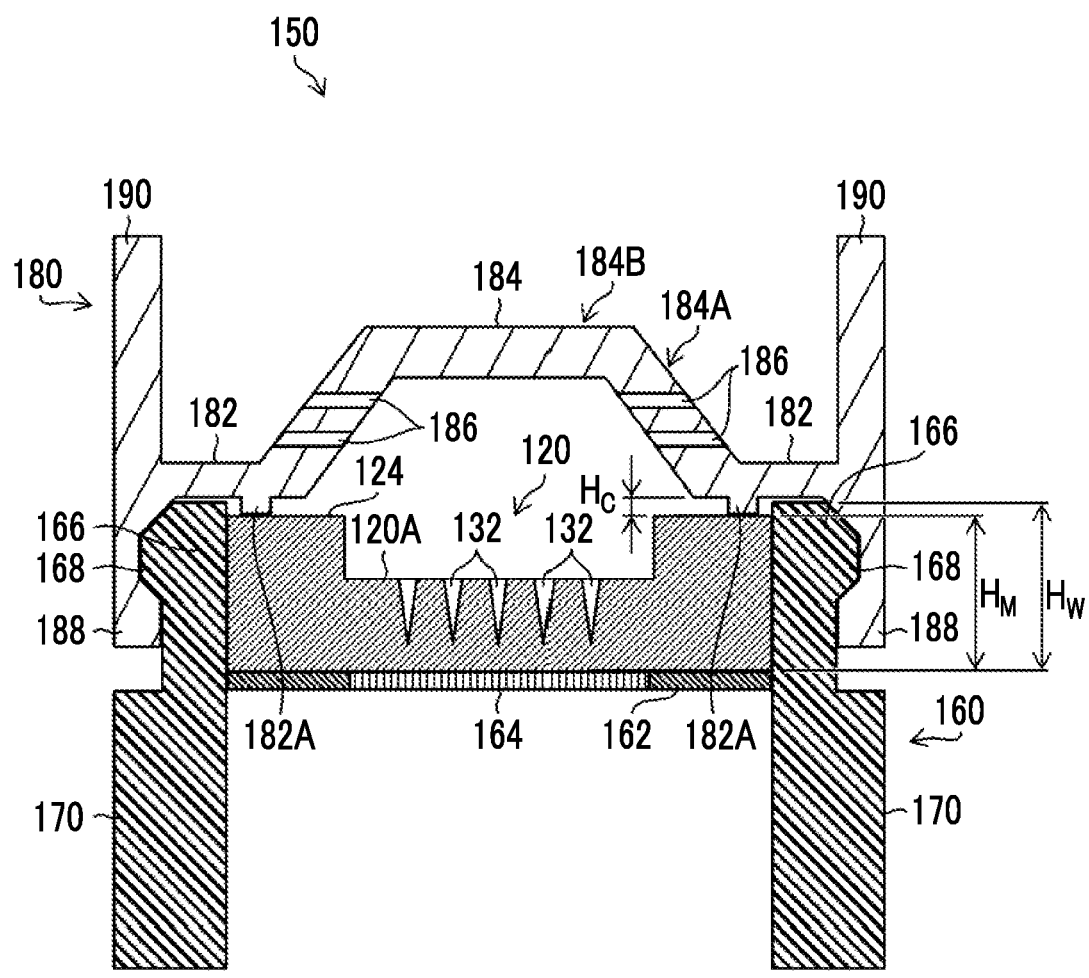
FIG. 8 is a cross-sectional view of a state where the lid is attached to the pedestal.

The protruding portion 182A is erected in a ring shape along the mold fixing portion 182 on the lower surface side of the mold fixing portion 182 in FIG. 8. At least a part of the protruding portion 182A faces the seating surface portion 162 in a case where the lid 180 is attached to the pedestal 160.

When it is assumed that the height of the protruding portion 182A is $H_C$, the thickness and the heights have a relationship of $H_C \geq H_W - H_M$. Therefore, in a case where the lid 180 is attached to the pedestal 160 on which the mold 120 is placed, the protruding portion 182A abuts the entire circumference of the bank portion 124 without bringing the mold fixing portion 182 and the upper surface of the side wall portion 166 in FIG. 8 into contact with each other. Accordingly, the bank portion 124, which is the edge portion of the mold 120, can be sandwiched between the seating surface portion 162 and the protruding portion 182A of the mold fixing portion 182.

Manufacturing Method of Percutaneous Absorption Sheet

FIG. 9 is a flowchart showing each step of a manufacturing method of the percutaneous absorption sheet 100. The manufacturing method of the percutaneous absorption sheet 100 includes a filling step (step S1), a lid attaching step (step S2), an evaporation and drying step (step S3), and a releasing step (step S4).

Filling Step (Step S1)

In the filling step, the needle-like recessed portions 132 of the mold 120 placed on the pedestal 160 are filled with a drug solution which is a liquid material. In the filling step, the lid 180 is not used.

The drug solution contains a drug stock solution as the drug (active ingredient), saccharides, an additive, and the like. The drug solution further contains water, ethanol, or the like as a solvent. Filling of the drug solution is performed by ejection by an ink jet head, spotting by a spotting head, dropwise addition by a dispenser, or the like.

Lid Attaching Step (Step S2)

In the lid attaching step, the lid 180 is attached to the pedestal 160 on which the mold 120 having completed the filling step is placed. In this embodiment, as the fixed engagement portion 168 and the elastic engagement portion 188 are engaged with each other in a snap-fit manner, the pedestal 160 and the lid 180 are fixed. Accordingly, the mold 120 enters a state of being stored in the mold case 150.

Evaporation and Drying Step (Step S3)

In the evaporation and drying step, the filled drug solution is evaporated and dried in a state where the mold 120 is stored in the mold case 150. The evaporation and drying step is preferably performed in a drying cabinet capable of adjusting the temperature and humidity.

When the lid 180 is attached to the pedestal 160, the mold fixing portion 182 abuts the entire circumference of the bank portion 124, which is the edge portion of the mold 120, and the bank portion 124, which is the edge portion of the mold 120, is sandwiched between the seating surface portion 162 of the pedestal 160 and the mold fixing portion 182 of the lid 180. Therefore, deformation of the mold 120 can be prevented while controlling the drying rate to an appropriate rate in the evaporation and drying step.

Releasing Step (Step S4)

In the releasing step, the sheet (percutaneous absorption sheet 100) formed through the evaporation and drying step is released from the mold 120.

As described above, according to the manufacturing method of the percutaneous absorption sheet 100, by using the mold case 150, the percutaneous absorption sheet 100 can be manufactured while preventing deformation of the percutaneous absorption sheet 100 while covering the front surface 120A of the mold 120.

The filling step is preferably performed under a sterile environment. In this case, it is necessary to sterilize the mold 120 and the mold case 150 before carrying the mold 120 and the mold case 150 in a sterile environment.

FIG. 10 is a schematic view illustrating a sterilization process. FIG. 10 illustrates a sterilization process using an autoclave 60. The autoclave 60 performs sterilization by raising the internal pressure with high-temperature steam. By disposing the mold case 150 in the autoclave 60, a high-pressure steam sterilization treatment can be performed.

In the example illustrated in FIG. 10, the lid 180 is placed on the pedestal 160 with the lid 180 turned upside down. That is, the hinge lever 190 is in a state of being supported by the fixed engagement portion 168. By placing the lid 180 in this manner, sterilized steam easily flows around the mold 120 inside the mold case 150, and an effect of improving drying properties is achieved.

Second Embodiment

A mold case 200 according to a second embodiment will be described. Like parts which are common to the mold case 150 are denoted by like reference numerals, and detailed descriptions thereof will be omitted.

Figure 11:
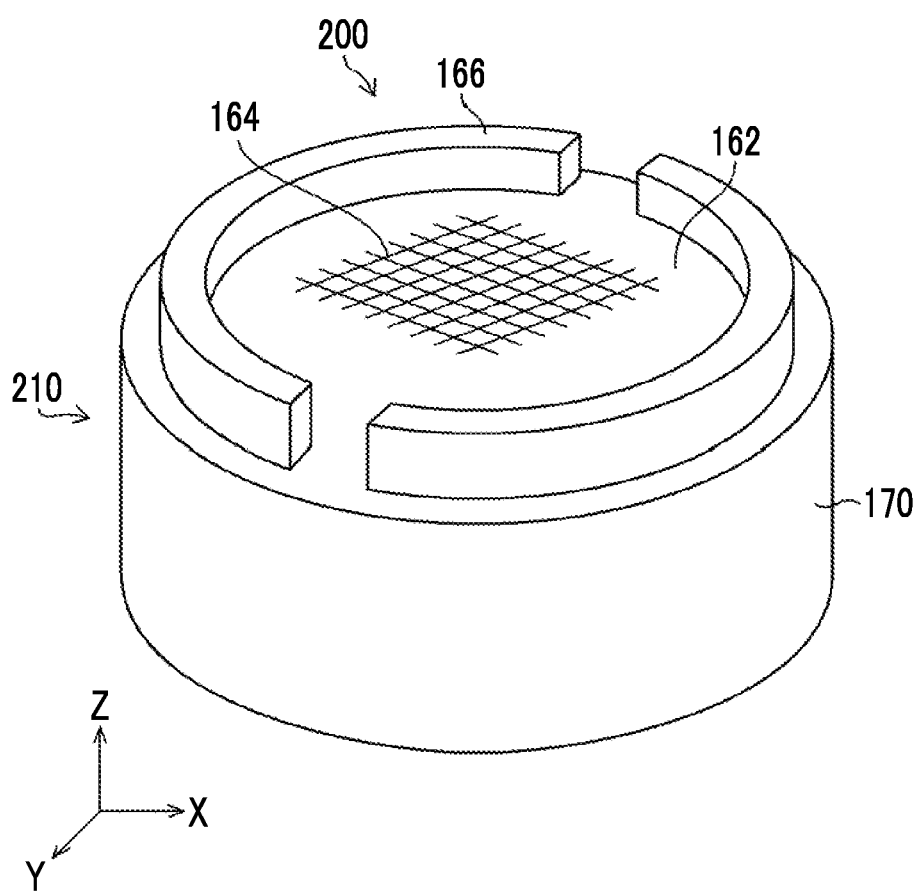
FIG. 11 is a perspective view of a pedestal.

FIG. 11 is a perspective view of a pedestal 210 of the mold case 200. The pedestal 210 includes the seating surface portion 162, the ventilation portion 164, the side wall portions 166, and the base portion 170. Unlike the pedestal 160, the fixed engagement portion 168 is not provided on the outer peripheral surface of the side wall portion 166 of the pedestal 210. The outer peripheral surface of the side wall portion 166 is provided parallel to the Z direction along the inner peripheral surface.

Figure 12:
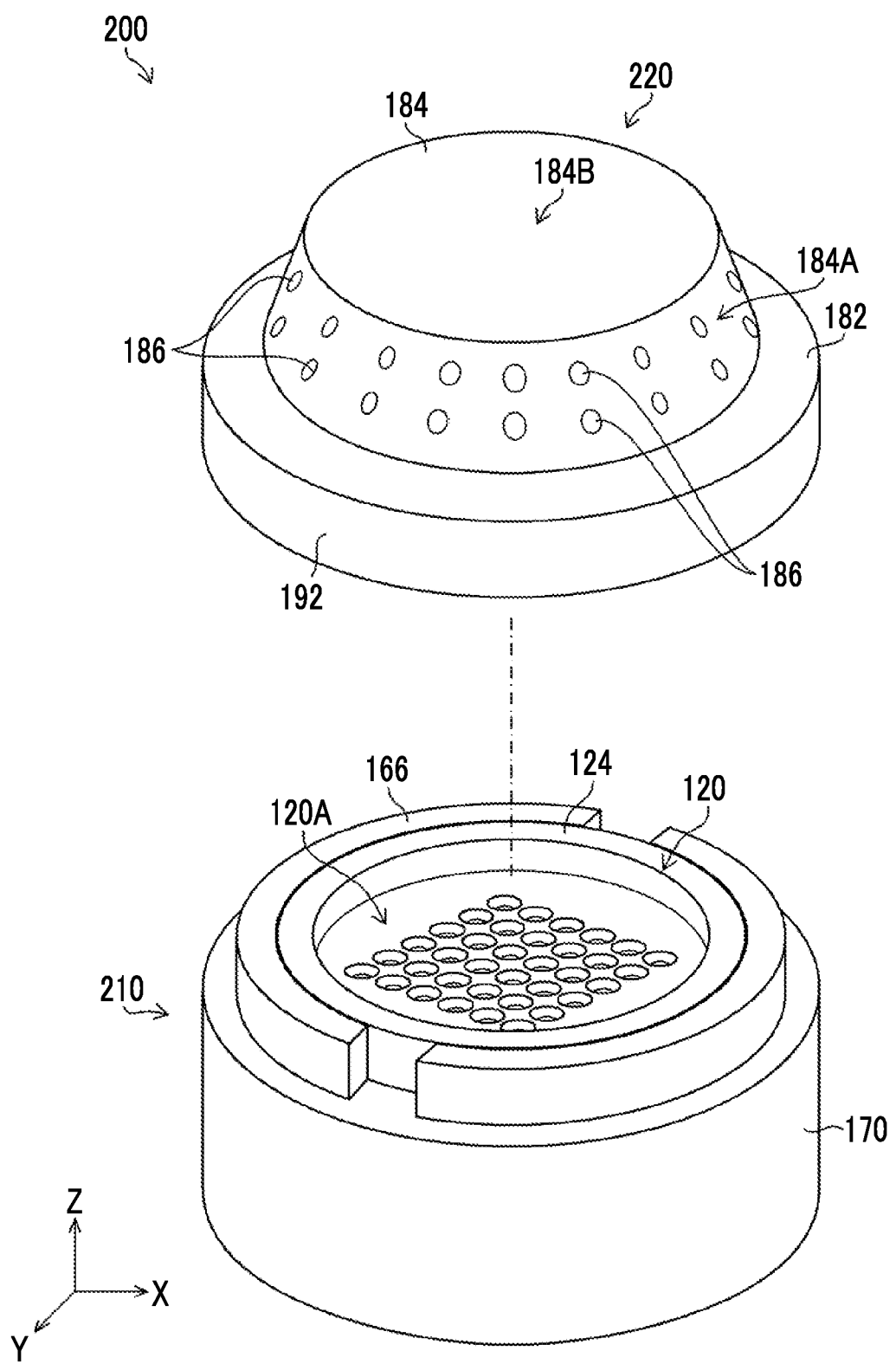
FIG. 12 is a perspective view illustrating the pedestal on which the mold is placed, and a lid.
Figure 13:
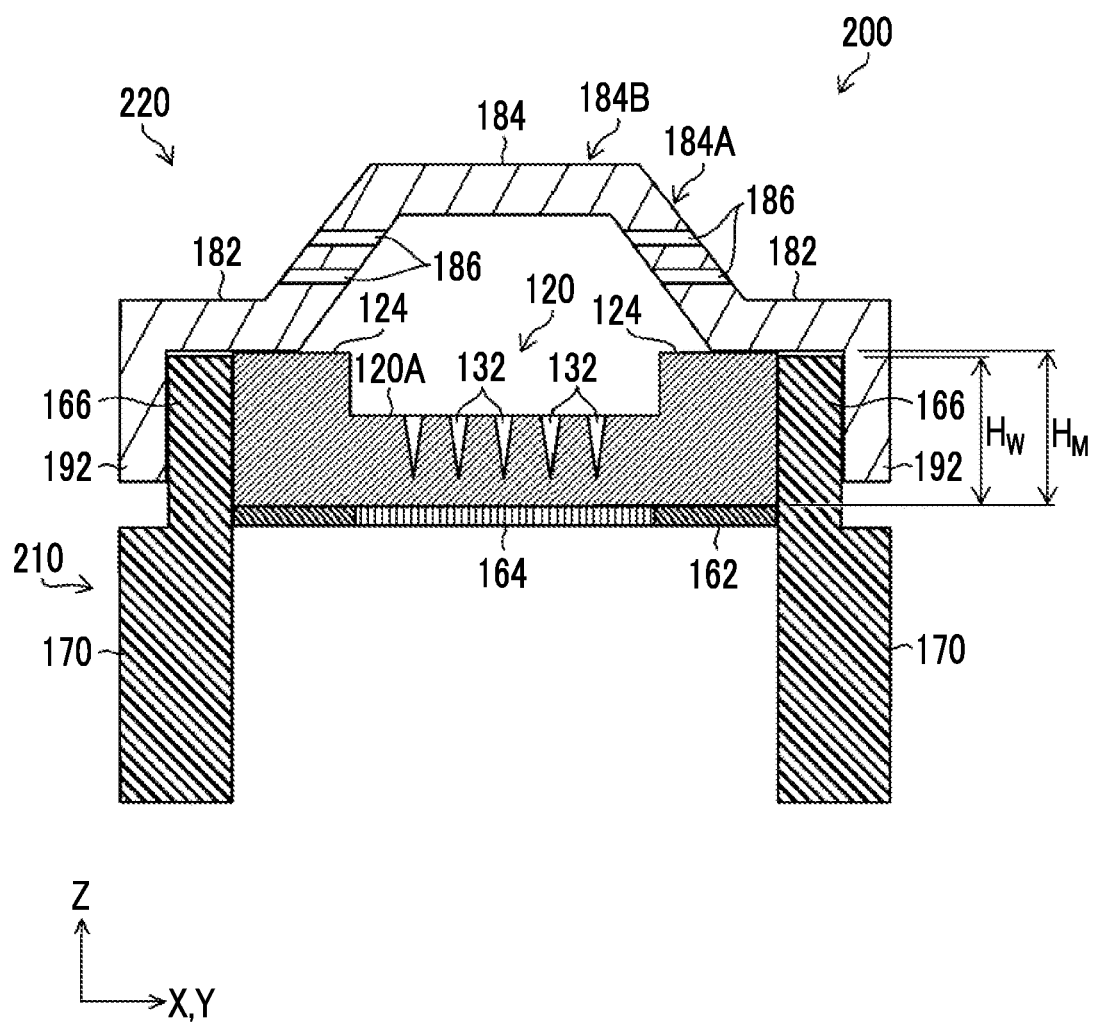
FIG. 13 is a cross-sectional view illustrating a state where the lid is attached to the pedestal.

FIG. 12 is a perspective view illustrating the pedestal 210 on which the mold 120 is placed, and a lid 220. FIG. 13 is a cross-sectional view illustrating a state where the lid 220 is attached to the pedestal 210.

The lid 220 includes the mold fixing portion 182, the cover portion 184, the through-holes 186, a cylindrical portion 192, and the like.

The cylindrical portion 192 is connected to the outer diameter side of the mold fixing portion 182 and is provided on the side opposite to the cover portion 184 with respect to the mold fixing portion 182. The inner diameter of the cylindrical portion 192 is coincident with the outer diameter of the side wall portion 166 of the pedestal 210. Therefore, the inner periphery of the cylindrical portion 192 and the outer periphery of the side wall portion 166 are brought into contact with each other, and the lid 220 and the pedestal 210 are fitted and fixed to each other.

Like the mold case 150, the side wall portion 166 is erected to be a height lower than the thickness of the mold 120. That is, assuming that the thickness (height) of the mold 120 is $H_M$ and the height of the side wall portion 166 from the seating surface portion 162 is $H_W$, the thickness and the height have a relationship of $H_M \geq H_W$. Accordingly, in a case where the lid 220 is attached to the pedestal 210, the bank portion 124, which is the edge portion of the mold 120, can be sandwiched between the seating surface portion 162 of the pedestal 210 and the mold fixing portion 182 of the lid 220.

Third Embodiment

A mold case 230 according to a third embodiment will be described. Like parts which are common to the mold case 200 are denoted by like reference numerals, and detailed descriptions thereof will be omitted.

Figure 14:
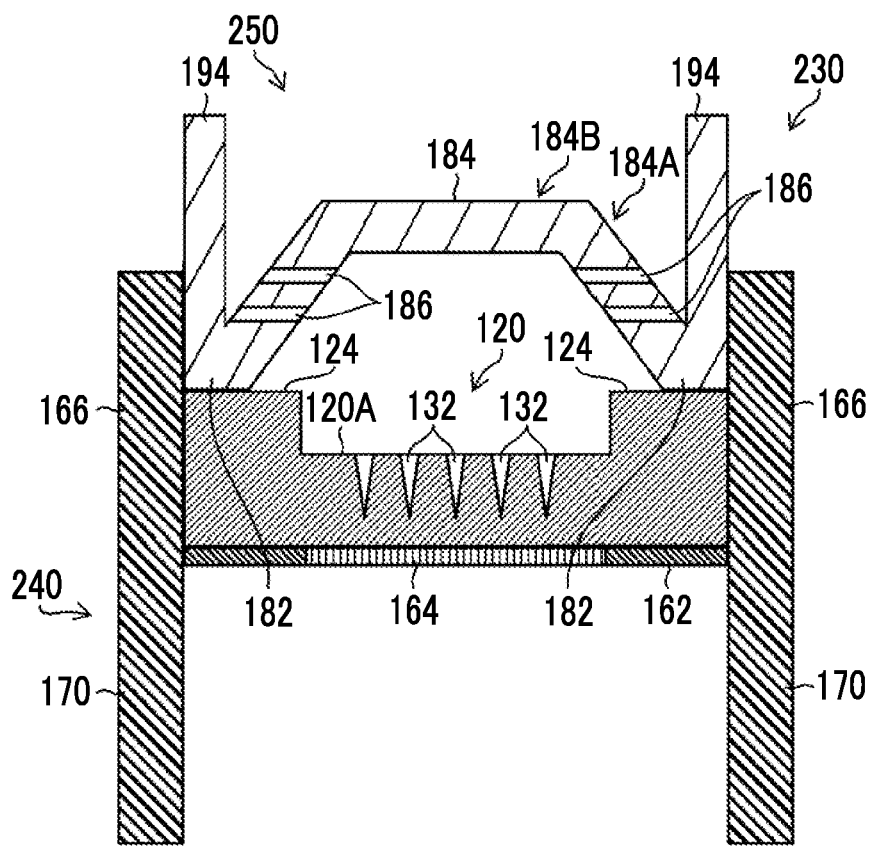
FIG. 14 is a cross-sectional view illustrating a state where a lid is attached to a pedestal.

FIG. 14 is a view illustrating the mold case 230. The mold case 230 is provided with a pedestal 240 and a lid 250. FIG. 14 illustrates a state where the lid 250 is attached to the pedestal 240 on which the mold 120 is placed.

The side wall portion 166 and the base portion 170 of the pedestal 240 are integrated cylindrical members having the same diameter, in which the side higher than the seating surface portion 162 in the Z direction is the side wall portion 166, and the lower side in the Z direction is the base portion 170. The side wall portion 166 is erected to be a height higher than the thickness of the mold 120.

The lid 250 includes the mold fixing portion 182, the cover portion 184, the through-holes 186, and a cylindrical portion 194.

The cylindrical portion 194 has a cylindrical shape, and the lower end thereof in the Z direction in FIG. 14 is connected to the mold fixing portion 182. The outer diameter of the cylindrical portion 194 is coincident with the inner diameter of the side wall portion 166 of the pedestal 240. Accordingly, the outer periphery of the cylindrical portion 194 and the inner periphery of the side wall portion 166 are brought into contact with each other, and the lid 250 and the pedestal 240 are fitted and fixed to each other.

In a state where the lid 250 is attached to the pedestal 240, the mold fixing portion 182 comes into contact with the bank portion 124, which is the edge portion of the mold 120. Therefore, the bank portion 124, which is the edge portion of the mold 120, can be sandwiched between the seating surface portion 162 of the pedestal 240 and the mold fixing portion 182 of the lid 250.

Fourth Embodiment

A mold case 260 according to a fourth embodiment will be described. Like parts which are common to the mold case 200 are denoted by like reference numerals, and detailed descriptions thereof will be omitted.

Figure 15:
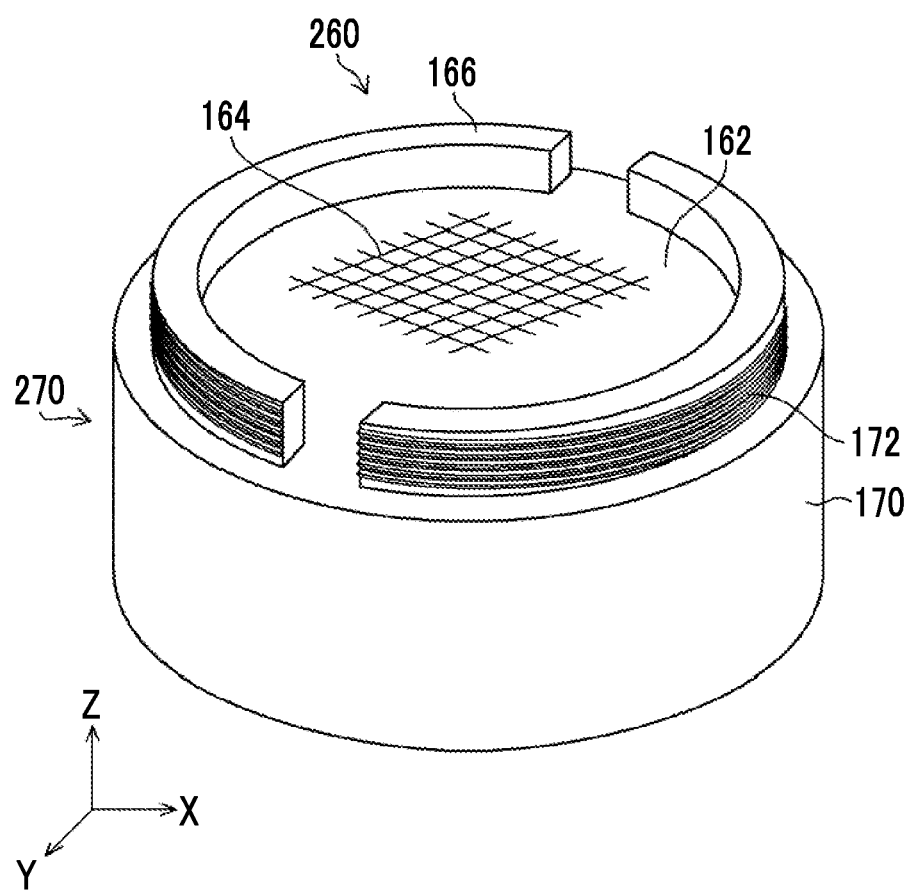
FIG. 15 is a perspective view of a pedestal.

FIG. 15 is a perspective view of a pedestal 270 of the mold case 260. The pedestal 270 includes the seating surface portion 162, the ventilation portion 164, the side wall portions 166, and the base portion 170. A male threaded portion 172 is provided on the outer peripheral surface of the side wall portion 166.

Figure 16:
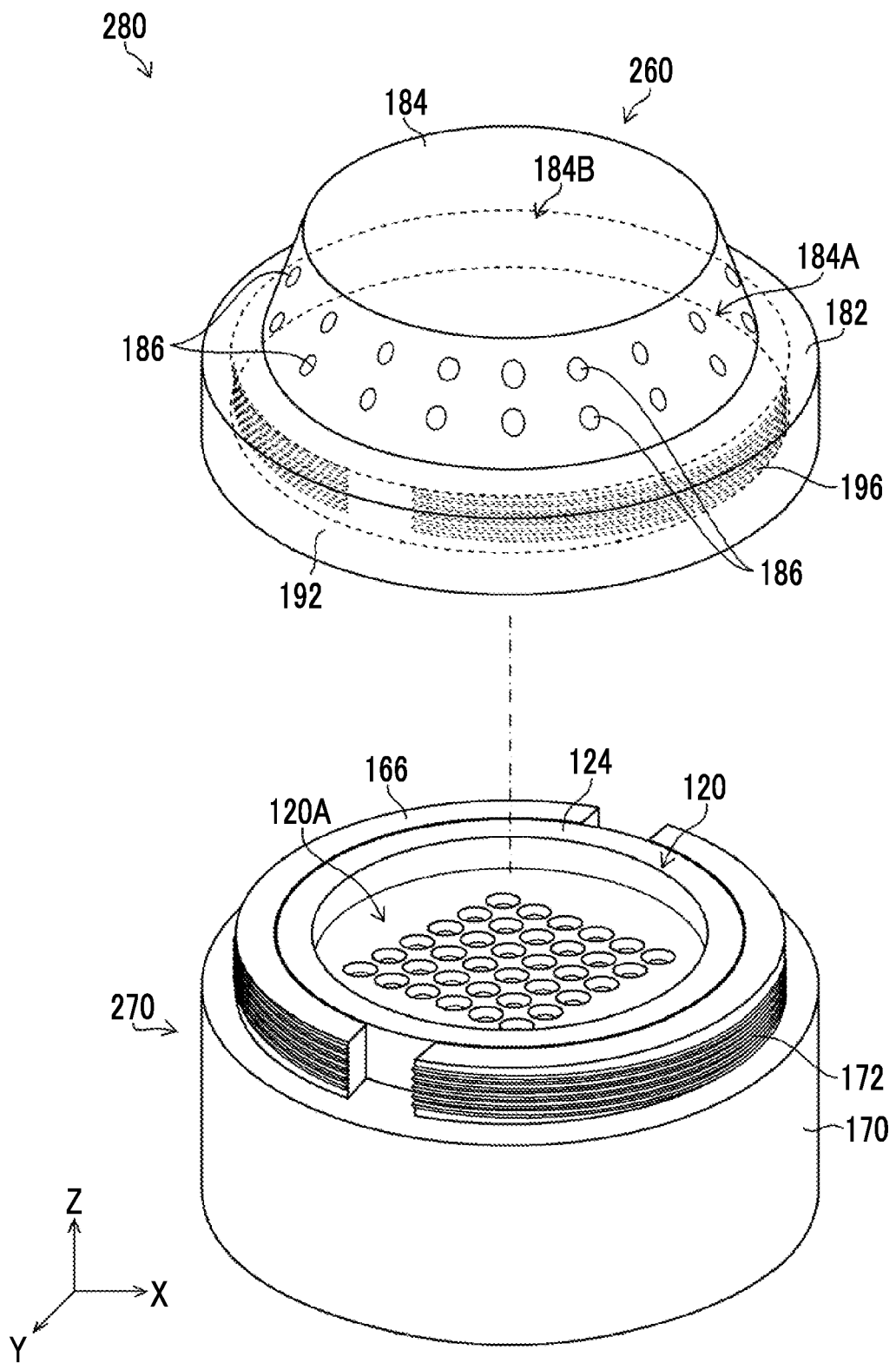
FIG. 16 is a perspective view illustrating the pedestal on which the mold is placed, and a lid.
Figure 17:
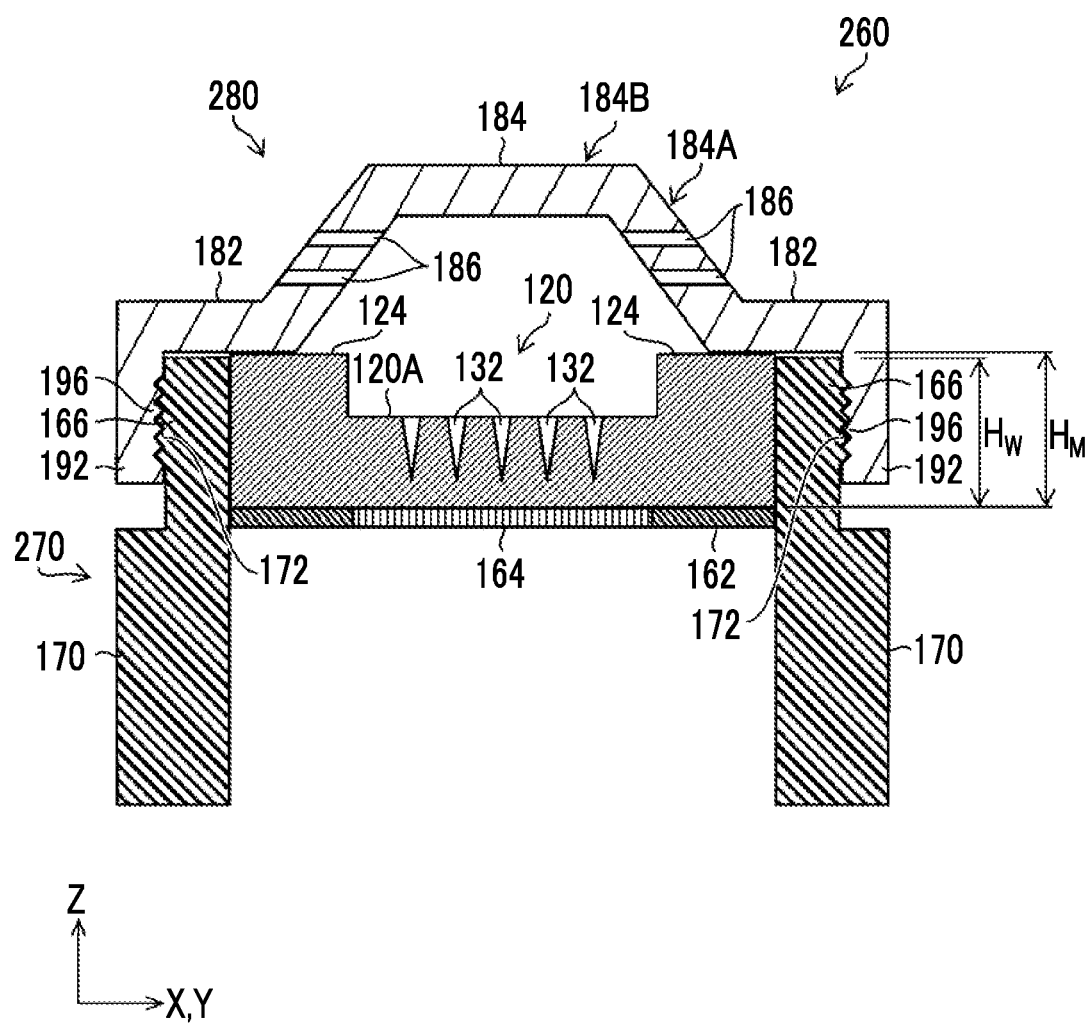
FIG. 17 is a cross-sectional view of a state where the lid is attached to the pedestal.

FIG. 16 is a perspective view illustrating the pedestal 270 on which the mold 120 is placed, and a lid 280. FIG. 17 is a cross-sectional view of a state where the lid 280 is attached to the pedestal 270.

The lid 280 includes the mold fixing portion 182, the cover portion 184, the through-holes 186, the cylindrical portion 192, and the like. The cylindrical portion 192 is connected to the outer diameter side of the mold fixing portion 182 and is provided on the side opposite to the cover portion 184 with respect to the mold fixing portion 182. A female threaded portion 196 is provided on the inner peripheral surface of the cylindrical portion 192. The female threaded portion 196 of the cylindrical portion 192 and the male threaded portion 172 of the outer peripheral surface of the side wall portion 166 of the pedestal 240 are configured to be screwed to each other. Accordingly, the lid 280 and the pedestal 270 are screwed and fixed to each other.

Like the mold case 200, the side wall portion 166 is erected to be a height lower than the thickness of the mold 120. Accordingly, the bank portion 124, which is the edge portion of the mold 120, can be sandwiched between the seating surface portion 162 of the pedestal 270 and the mold fixing portion 182 of the lid 280.

Fifth Embodiment

A mold case 290 according to a fifth embodiment will be described. Like parts which are common to the mold case 230 are denoted by like reference numerals, and detailed descriptions thereof will be omitted.

Figure 18:
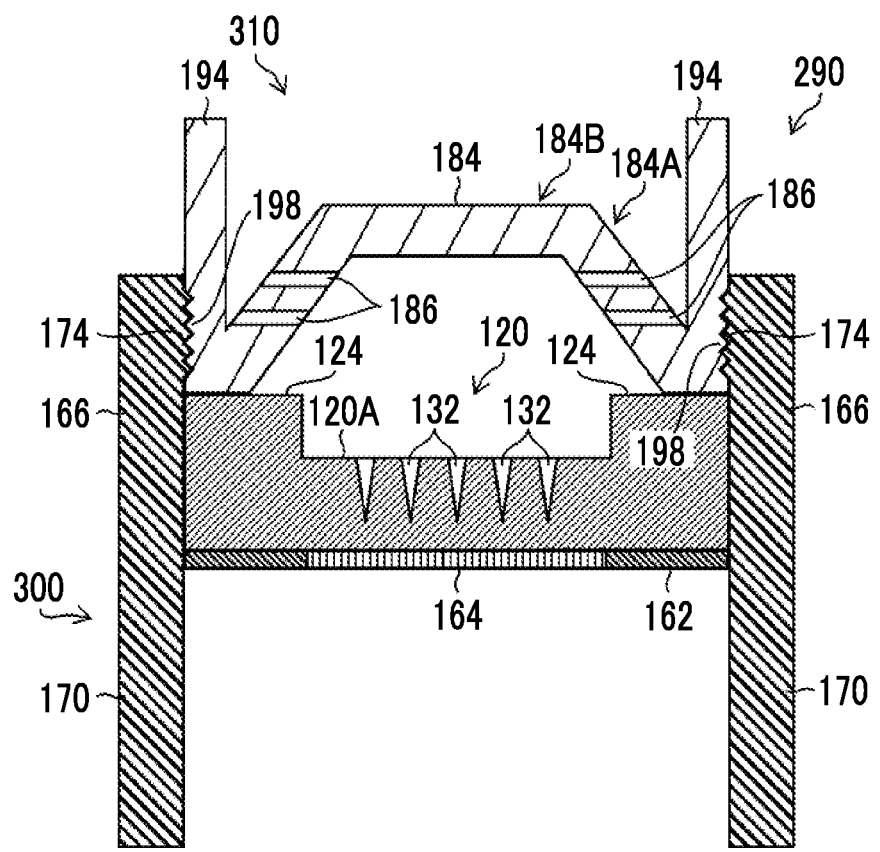
FIG. 18 is a cross-sectional view illustrating a state where a lid is attached to a pedestal.

FIG. 18 is a view illustrating the mold case 290. The mold case 290 is provided with a pedestal 300 and a lid 310. FIG. 18 illustrates a state where the lid 310 is attached to the pedestal 300 on which the mold 120 is placed.

The side wall portion 166 and the base portion 170 of the pedestal 300 are integrated cylindrical members having the same diameter, in which the side higher than the seating surface portion 162 in the Z direction is the side wall portion 166, and the lower side in the Z direction is the base portion 170. The side wall portion 166 is erected to be a height higher than the thickness of the mold 120. A female threaded portion 174 is provided on the inner peripheral surface of the side wall portion 166.

The lid 310 includes the mold fixing portion 182, the cover portion 184, the through-holes 186, the cylindrical portion 194, and the like.

The cylindrical portion 194 has a cylindrical shape, and the lower end thereof in the Z direction in FIG. 18 is connected to the mold fixing portion 182. A male threaded portion 198 is provided on the outer peripheral surface of the cylindrical portion 194. The male threaded portion 198 of the cylindrical portion 194 and the female threaded portion 174 of the inner peripheral surface of the side wall portion 166 of the pedestal 300 are configured to be screwed to each other. Accordingly, the lid 310 and the pedestal 300 are screwed and fixed to each other.

In a state where the lid 310 is attached to the pedestal 300, the mold fixing portion 182 comes into contact with the bank portion 124, which is the edge portion of the mold 120. Therefore, the bank portion 124, which is the edge portion of the mold 120, can be sandwiched between the seating surface portion 162 of the pedestal 300 and the mold fixing portion 182 of the lid 310.

Sixth Embodiment

A mold case 320 according to a sixth embodiment will be described. Like parts which are common to the mold case 200 are denoted by like reference numerals, and detailed descriptions thereof will be omitted.

Figure 19:
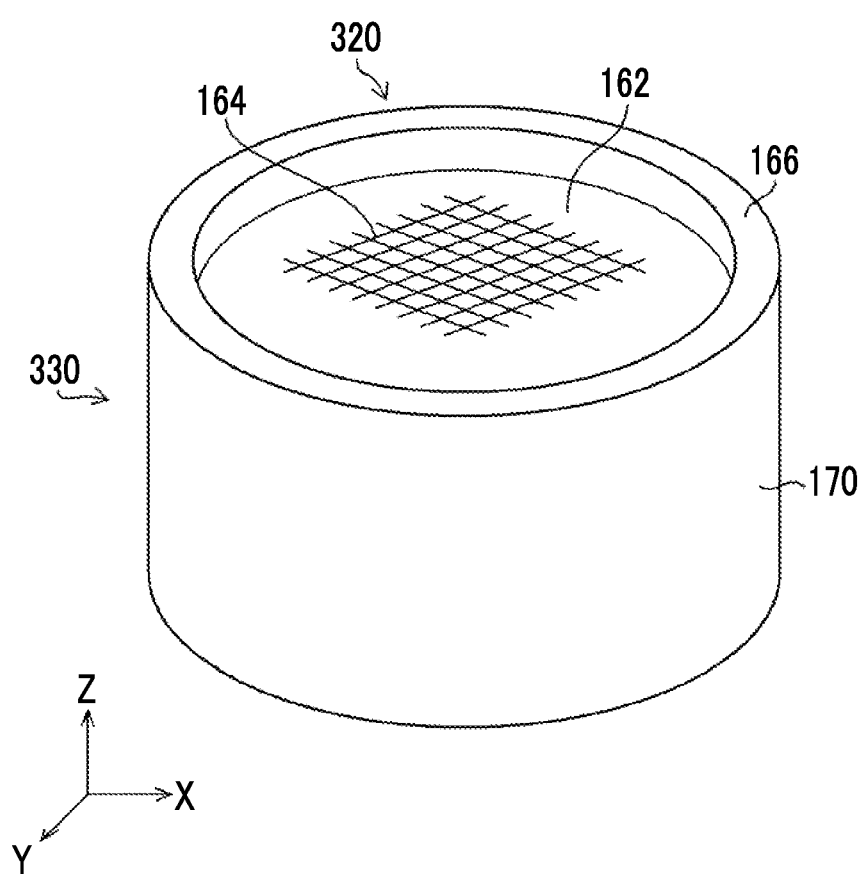
FIG. 19 is a perspective view of a pedestal.

FIG. 19 is a perspective view of a pedestal 330 of the mold case 320. The pedestal 330 includes the seating surface portion 162, the ventilation portion 164, the side wall portion 166, and the base portion 170. The side wall portion 166 and the base portion 170 are integrated cylindrical members having the same diameter, in which the side higher than the seating surface portion 162 in the Z direction is the side wall portion 166, and the lower side in the Z direction is the base portion 170.

Figure 21:
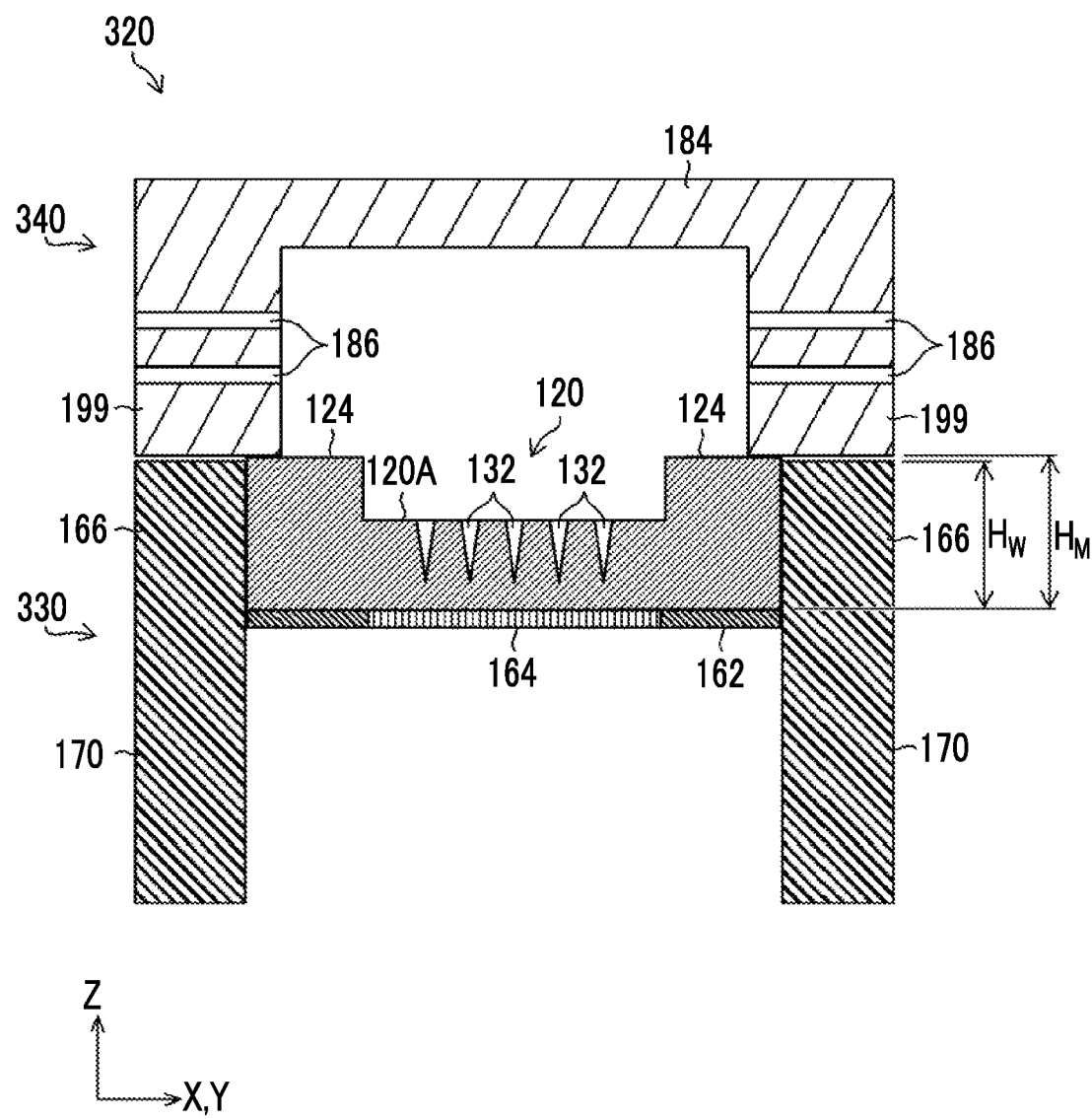
FIG. 21 is a cross-sectional view of a state where the lid is attached to the pedestal.

FIG. 20 is a perspective view illustrating the pedestal 330 on which the mold 120 is placed, and a lid 340. FIG. 21 is a cross-sectional view of a state where the lid 340 is attached to the pedestal 330.

The lid 340 includes the cover portion 184, the through-holes 186, and a cylindrical portion 199. The cylindrical portion 199 has a cylindrical shape having a constant thickness, and the cover portion 184 is provided at an end on the upper side in the Z direction. At least a part of the cylindrical portion 199 faces the seating surface portion 162 in a state where the lid 340 is attached to the pedestal 330.

The side wall portion 166 is erected to be a height lower than the thickness of the mold 120. As illustrated in FIG. 21, in a state where the lid 340 is attached to the pedestal 330, the cylindrical portion 199 of the lid 340 is placed on the bank portion 124, which is the edge portion of the mold 120, and is supported by the bank portion 124 of the mold 120 at the part of the cylindrical portion 199 facing the seating surface portion 162. That is, the cylindrical portion 199 functions as a mold fixing portion that abuts the entire circumference of the bank portion 124. Therefore, the bank portion 124, which is the edge portion of the mold 120, can be sandwiched between the seating surface portion 162 of the pedestal 330 and the cylindrical portion 199 of the lid 340.

The lid 340 preferably has a mass of 4 grams or more, and more preferably has a mass of 5 grams or more. Accordingly, deformation of the mold 120 can be appropriately prevented.

Furthermore, in a case where the mass of the lid 340 is large, in a case where the filling amount of the drug solution is managed by mass, there is a problem that the measurement accuracy deteriorates. In addition, the balance of the mold case 320 becomes worse, and there is a risk that the mold case 320 may fall over during carrying. Therefore, the lid 340 preferably has a mass of 20 grams or less, and more preferably 10 grams or less.

EXPLANATION OF REFERENCES

60: autoclave
100: percutaneous absorption sheet
100A: front surface
100B: rear surface
102: sheet portion
110: protruding pattern
112: needle-like protruding portion
114: needle portion
116: frustum portion
120: mold
120A: front surface
120B: rear surface
122: flat portion
124: frustum portion
130: recessed portioned pattern
132: needle-like recessed portion
134: distal end recessed portion
136: cup portion
150: mold case
160: pedestal
162: seating surface portion
164: ventilation portion
166: side wall portion
168: fixed engagement portion
170: base portion
172: male threaded portion
174: female threaded portion
180: lid
182: mold fixing portion
184: cover portion
184A: conical surface
184B: top surface
186: through-hole
188: elastic engagement portion
190: hinge lever
192: cylindrical portion
194: cylindrical portion
196: female threaded portion
198: male threaded portion
199: cylindrical portion
200: mold case
210: pedestal
220: lid
230: mold case
240: pedestal
250: lid
260: mold case
270: pedestal
280: lid
290: mold case
300: pedestal
310: lid
320: mold case
330: pedestal
340: lid
S1 to S4: steps of manufacturing method of percutaneous absorption sheet

What is claimed is:

1. A mold case comprising:
a pedestal which supports a rear surface of a mold that has flexibility and has a plurality of needle-like recessed portions on a front surface; and
a lid which is attachable to and detachable from the pedestal and covers the front surface of the mold,
wherein the lid causes only an edge portion of the mold to be sandwiched between the lid and the pedestal.

2. The mold case according to claim 1,
wherein the pedestal includes a seating surface portion on which the mold is placed, and
the lid includes a mold fixing portion at least a part of which is parallel to and faces the seating surface portion.

3. The mold case according to claim 2,
wherein the mold fixing portion abuts the mold over an entire circumference of the edge portion of the mold.

4. The mold case according to claim 2,
wherein the lid includes a cover portion which is connected to the mold fixing portion and forms a space between the cover portion and the plurality of needle-like recessed portions.

5. The mold case according to claim 2,
wherein the pedestal includes a side wall portion which is erected on the seating surface portion and surrounds the mold placed on the seating surface portion.

6. The mold case according to claim 5,
wherein the side wall portion is erected to be a height lower than a thickness of the mold.

7. The mold case according to claim 5, further comprising:
a fixed engagement portion provided on an outer peripheral surface of the side wall portion of the pedestal; and
an elastic engagement portion provided in the mold fixing portion of the lid,
wherein the pedestal and the lid are fixed to each other by snap-fit engagement between the fixed engagement portion and the elastic engagement portion.

8. The mold case according to claim 7,
wherein, in the lid, a hinge lever that releases the snap-fit engagement is provided in the mold fixing portion.

9. The mold case according to claim 5,
wherein the lid includes a tubular portion connected to the mold fixing portion, and
the tubular portion and the side wall portion are brought into contact with each other to be fitted and fixed to each other.

10. The mold case according to claim 5,
wherein the side wall portion and the mold fixing portion are screwed and fixed to each other.

11. The mold case according to claim 1,
wherein the lid has a mass of 4 grams or more, and
the lid is supported by the edge portion of the mold.

12. The mold case according to claim 1,
wherein the mold has a bank portion provided at the edge portion of the front surface, and
the lid causes the bank portion of the mold to be sandwiched between the lid and the pedestal.

* * * * *